(12) United States Patent
Bombardelli

(10) Patent No.: US 10,286,028 B2
(45) Date of Patent: May 14, 2019

(54) **COMPOSITIONS CONTAINING EXTRACTS OF *CURCUMA LONGA* AND *ECHINACEA ANGUSTIFOLIA* WHICH ARE USEFUL TO REDUCE PERIPHERAL INFLAMMATION AND PAIN**

(71) Applicant: INDENA S.P.A., Milan (IT)

(72) Inventor: Ezio Bombardelli, Gropello Cairoli (IT)

(73) Assignee: INDENA S.P.A., Milan (IT)

( * ) Notice: Subject to any disclaimer, the term of this patent is extended or adjusted under 35 U.S.C. 154(b) by 0 days.

(21) Appl. No.: 15/118,861

(22) PCT Filed: Feb. 18, 2015

(86) PCT No.: PCT/EP2015/053399
§ 371 (c)(1),
(2) Date: Aug. 13, 2016

(87) PCT Pub. No.: WO2015/124616
PCT Pub. Date: Aug. 27, 2015

(65) Prior Publication Data
US 2017/0049840 A1    Feb. 23, 2017

(30) Foreign Application Priority Data
Feb. 20, 2014 (IT) .............................. MI2014A0251

(51) Int. Cl.
| | |
|---|---|
| A61K 36/9066 | (2006.01) |
| A61K 36/758 | (2006.01) |
| A61K 31/12 | (2006.01) |
| A61K 31/685 | (2006.01) |
| A61K 36/28 | (2006.01) |
| A61K 9/00 | (2006.01) |
| A61K 47/10 | (2017.01) |
| A61K 47/14 | (2017.01) |
| A61K 9/20 | (2006.01) |
| A61K 9/48 | (2006.01) |
| A61K 47/54 | (2017.01) |

(52) U.S. Cl.
CPC ........ *A61K 36/9066* (2013.01); *A61K 9/0014* (2013.01); *A61K 9/0053* (2013.01); *A61K 9/2009* (2013.01); *A61K 9/2018* (2013.01); *A61K 9/2054* (2013.01); *A61K 9/4858* (2013.01); *A61K 31/12* (2013.01); *A61K 31/685* (2013.01); *A61K 36/28* (2013.01); *A61K 36/758* (2013.01); *A61K 47/10* (2013.01); *A61K 47/14* (2013.01); *A61K 47/544* (2017.08); *A61K 2236/37* (2013.01)

(58) Field of Classification Search
None
See application file for complete search history.

(56) References Cited

U.S. PATENT DOCUMENTS 6,440,448 B1    8/2002    Intelisano

FOREIGN PATENT DOCUMENTS

| CN | 101607068 A | 12/2009 |
|---|---|---|
| EP | 0464298 A1 | 1/1992 |
| EP | 1837030 A1 | 9/2007 |
| EP | 2014295 A2 | 1/2009 |
| JP | 2006347948 A | 12/2006 |
| WO | 2000002570 A1 | 1/2000 |
| WO | 2009061152 A2 | 5/2009 |
| WO | 2012013551 A1 | 2/2012 |

OTHER PUBLICATIONS

BelCaro (Alternative Medicine Review (2010), vol. 15, No. 4, pp. 337-344).*
Search and Written Opinion of PCT/EP2015/053399 dated May 26, 2015.
Communication of foreign counsel regarding for corresponding Singapore Patent Application No. 11201606831P entitled Compositions Containing Extracts of Curcuma Longa and Echinacea Angustifolia Which Are Useful to Reduce Peripheral Inflammation and Painin the name Indena S.p.A.National Phase of: PCT/EP2015/053399, dated Sep. 12, 2017.
Office Action for corresponding Singapore patent application 11201606831P dated Sep. 5, 2017.
Tu Feng & Liu Yi Zheng, "Cervical Spondylosis: TCM* Treatment and After Care" Chapter 3: Acupuncture and tuina to treat cervical spondylosis p. 67, Dec. 1, 2013.

* cited by examiner

*Primary Examiner* — Susan Hoffman
(74) *Attorney, Agent, or Firm* — Silvia Salvadori, P.C.; Silvia Salvadori

(57) ABSTRACT

The present invention relates to compositions containing, as their only active ingredients, an extract of *Curcuma* spp, optionally as curcumin in the form of a complex with phospholipids, and an extract selected from *Echinacea* spp extract or lipophilic extract of *Zanthoxylum* spp, which are useful in the topical and systemic treatment of peripheral pain and of superficial and deep inflammatory and painful conditions. The compositions according to the invention are particularly effective in the treatment of osteoarthritis and rheumatoid arthritis in patients unable to tolerate long-term treatment with NSAIDs or steroids.

5 Claims, No Drawings

COMPOSITIONS CONTAINING EXTRACTS OF *CURCUMA LONGA* AND *ECHINACEA ANGUSTIFOLIA* WHICH ARE USEFUL TO REDUCE PERIPHERAL INFLAMMATION AND PAIN

This application is a U.S. national stage of PCT/EP2015/053399 filed on 18 Feb. 2015, which claims priority to and the benefit of Italian Application No. MI2014A000251 filed on 20 Feb. 2014, the contents of which are incorporated herein by reference in their entireties.

SUMMARY OF THE INVENTION

The present invention relates to compositions containing, as their only active ingredients, an extract of *Curcuma* spp, optionally as curcumin in the form of a complex with phospholipids, and an extract selected from *Echinacea* spp extract or a lipophilic extract of *Zanthoxylum* spp, which are useful in the topical and systemic treatment of peripheral pain and of superficial and deep inflammatory and painful conditions. The compositions according to the invention are particularly effective in the treatment of osteoarthritis and rheumatoid arthritis in patients unable to tolerate long-term treatment with NSAIDs or steroids.

STATE OF THE ART

Osteoarthritis is one of the major causes of physical disability in elderly people. As well as reducing the quality of life of millions of individuals all over the world, it also causes financial loss to both families and the community, because the costs of the care involved are very high.

Conventional treatments for osteoarthritis involve symptomatic treatment with analgesics and therapeutic treatment with non-steroidal anti-inflammatory drugs, which are known to induce serious side effects that often lead to discontinuance of the treatment. Similar considerations also apply to rheumatoid arthritis. For these reasons, research has also focused on phytotherapy medicaments and natural plant remedies in general.

Lipophilic extracts and alcoholic extracts of *Echinacea* spp. possess both topical and systemic anti-inflammatory activity attributable to their isobutylamide content, isobutylamides being ligands of the CB1 and CB2 cannabinoid receptors and vanilloid receptor TRPV1. The lipophilic extracts of *Echinacea angustifolia* described in EP 0464298 are particularly effective in this respect, due to their high isobutylamide content.

The roots and rhizomes of turmeric (*Curcuma*) have been used as spices in India since time immemorial, and are also used in many industrialised countries today. Its active constituent is curcumin, the yellow compound that constitutes the main ingredient of curry and other traditional Indian dishes. The uses described in traditional medicine include the treatment of indigestion, flatulence and diarrhoea, and especially of inflammatory conditions and joint pain after long-term treatment. Many of these traditional uses have been confirmed by in vitro biochemical tests or pharmacology.

Curcumin is now one of the molecules most frequently investigated from the biochemical standpoint, and in recent years, as well as numerous publications of doubtful scientific value, controlled double-blind clinical trials have also been conducted according to the protocols of modern clinical pharmacology. Preliminary clinical trials have demonstrated the low bioavailability of the molecule, which is unstable at intestinal pH (half-life at pH 7<10 min), and its low oral absorption, which limit many of the applications indicated by the in vitro tests. Plasma concentrations of 50 ng are reported after administration of 12 g of compound, the secondary metabolites, glucuronides and sulphates also being measured.

Like many polyphenols, curcumin is poorly soluble in water and fats. The Applicant has therefore devised a patent WO2007101551 that describes its complexing with phospholipids to improve its bioavailability. Curcumin in phospholipid-complexed form provides improved systemic and topical absorption, which allows it to be administered to humans.

Clinical trials conducted on patients with osteoarthritis have demonstrated that long-term treatment with phospholipid-complexed curcumin (Belcaro et al, Alternative Medicine Review, 4, 338, 2010) gives favourable but still insufficient results due to the low level of pain reduction, which obliges patients to take NSAIDs.

However, significant improvements were only obtained after 8 months' treatment, and many patients had to use NSAIDs or other analgesics to alleviate the pain.

DESCRIPTION OF THE INVENTION

It has now surprisingly been found that compositions containing as the only active ingredients *Curcuma* spp extract and an extract selected from *Echinacea* spp extract or lipophilic extract of *Zanthoxylum* spp possess potent analgesic and anti-inflammatory activity, which is greater than that found when the extracts are used separately.

Particularly favourable results have been observed with compositions containing phospholipid-complexed curcumin and lipophilic extracts of *Echinacea angustifolia*.

Good results have also been obtained by replacing the *Echinacea* extracts with extracts of other plants having a high isobutylamide content, especially lipophilic extract of *Zanthoxylum* spp.

The object of the invention is therefore compositions substantially consisting of an extract of *Curcuma* spp or curcumin, and an extract selected from *Echinacea angustifolia* extract or lipophilic extract of *Zanthoxylum bungeanum*, mixed with acceptable excipients.

The invention relates in particular to compositions substantially consisting of an extract of *Curcuma* spp or curcumin, and an extract selected from *Echinacea angustifolia* extract or lipophilic extract of *Zanthoxylum bungeanum*, mixed with acceptable excipients.

The compositions according to the invention may be administered orally or topically.

According to a preferred aspect, the compositions for oral administration will contain phospholipid-complexed curcumin in amounts ranging from 100 to 1000 mg, and *Echinacea* extract in amounts ranging from 1 to 200 mg, or alternatively lipophilic extract of *Zanthoxylum* spp. in amounts ranging from 5 to 25 mg per oral dose unit. According to a particularly preferred aspect, the compositions for oral administration will contain 500 mg of phospholipid-complexed curcumin and 5 mg of *Echinacea* extract, or alternatively 10 mg of lipophilic extract of *Zanthoxylum* spp., per oral dose unit.

According to a preferred aspect, the compositions for topical administration will contain phospholipid-complexed curcumin in amounts ranging from 0.1 to 0.5% by weight, and *Echinacea* extract in amounts ranging from 0.05 to 0.5% by weight, or alternatively lipophilic extract of *Zanthoxylum* spp in amounts ranging from 0.1 to 1% by weight. According to a particularly preferred aspect, the compositions for topical administration will contain 0.2% by weight of phospholipid-complexed curcumin, and 0.2% by weight of *Echinacea* extract, or alternatively 0.5% by weight of lipophilic extract of *Zanthoxylum* spp.

The compositions according to the invention can be used to treat peripheral pain of all kinds, ranging from diabetic neuropathy to joint and muscle pain of various origins. It is particularly important that the compositions according to the invention do not cause side effects in the gastrointestinal tract, to allow its use by patients with gastric problems who are unable to tolerate NSAIDs.

Lipophilic extracts of *Echinacea* spp can be obtained by extraction from the roots or rhizomes with alcohols, ketones or aliphatic ethers, or preferably with carbon dioxide under supercritical conditions in accordance with EP464298.

Alcoholic extracts of *Echinacea* spp still containing a pharmacologically active amount of isobutylamides have proved effective provided that at least a minimal dose of 1 mg of isobutylamine complex is administered to the patient. The active clinical doses range from 0.5 mg to 10 mg, preferably 5 mg for a mean body weight of 70 Kg.

The lipophilic extract of *Zanthoxylum* spp can be prepared in accordance with WO 00/02570.

However, the compositions according to the invention provide almost immediate relief of patients' symptoms, with no need to use other medicaments. Patients with gastro-oesophageal reflux and at the pre-ulcerative stage are also able to take the compositions according to the invention.

Pharmacological Tests

1. Tail-flick Test in the Rat

The analgesic activity of the compositions according to the invention (combination of phospholipid-complexed curcumin and *Echinacea* extract) was compared with that of the individual ingredients administered separately to rats. The results demonstrated a clear synergy between the two ingredients of the compositions according to the invention, as shown in Table 1 below.

The analgesic activity was evaluated with the tail-flick test in the rat. Before treatment, 3 basic measurements were conducted on the animals to ensure that they were suitable for the handling and apparatus involved. The parameters used were 15V of radiant heat and a 15-second cut-off (to prevent irreversible harm to the animals), with evaluation of the tail-flick. The animals were treated with 0.1 ml of ointment of the composition described in example 4, 5 cm from the base of the tail. The analgesic effect was measured 15 and 30 min. after administration.

The two individual ingredients of the composition were evaluated with the same experimental model, in two separate formulations which contained the same amount of one of the active ingredients as the composition described in example 4. The control animals were treated with 0.1 ml of the oil used to dissolve the two ingredients (carrier).

TABLE 1

| Treatment | Latency time | | | |
|---|---|---|---|---|
| | after 15 min | % increase | after 30 min | % increase |
| Carrier | 4.5 ± 0.33 | — | 4.6 ± 0.45 | — |
| Composition described in example 4 | 12.6 ± 0.61 | 180 | 8.5 ± 0.43 | 84.8 |
| *Echinacea angustifolia* lipophilic extract | 6.1 ± 0.44 | 35.5 | 4.8 ± 0.63 | 4.4 |
| Phospholipid-complexed curcumin | 4.2 ± 0.63 | — | 4.6 ± 0.48 | — |

2. Analgesic Activity in Humans 40 patients suffering from bone disease of the knee with constant pain were randomised and treated with two tablets a day according to Example 1, one in the morning and one in the evening, or with a placebo (consisting of the carrier only), or with the individual ingredients added to the placebo formulation at the same concentrations as in the formulation described in example 1.

Efficacy was scored on an international analogue pain scale with scores from 0 to 10, 10 points indicating maximum pain and 0 the disappearance of pain. The effect was evaluated on the second day after administration of the tablet, in the mornings 60 and 120 minutes after treatment.

The results are set out in Table 2 below.

TABLE 2

| Treatment | Pain scores at time | | |
|---|---|---|---|
| | 0 | 60 min | 120 min |
| Placebo | 8.3 ± 1.7 | 9.1 ± 2.2 | 8.2 ± 1.9 |
| Composition described in example 1 | 9.4 ± 2.6 | 4.3 ± 0.9 | 2.5 ± 1.4 |
| *Echinacea angustifolia* lipophilic extract | 8.7 ± 1.4 | 7.4 ± 1.2 | 7.1 ± 2.6 |
| Phospholipid-complexed curcumin | 8.2 ± 1.6 | 7.9 ± 0.6 | 8.6 ± 1.8 |

3. Effect on Osteoarthritis

Table 3 shows the results obtained, after treatment for up to three months with the composition according to the invention, on the global effect of osteoarthritis on the patients recruited, following the Karnofsky Scale for both selection and evaluation of efficacy (J.Clin.Oncology 1984; 2:187-193).

The evaluation was conducted by measuring the distance traveled without pain, and with different degrees of pain, on a treadmill set to 3 Km/h and an inclination of 10%. 80 patients suffering from osteoarthritis of the knee were divided into two groups. After randomisation, one group was treated with the placebo and the other with the composition described in example 1. Pain was evaluated weekly during the treatment with the WOMAC index, and the humoral parameters, which constitute indexes of inflammatory parameters, were evaluated every month. (Table 4).

TABLE 3

| | Results of distance travelled on treadmill | | |
|---|---|---|---|
| | Distance travelled at time | | |
| Treatment | 0 | 1 month | 3 months |
| Placebo | 84.6 metres | 90.1 metres | xx |
| Composition described in example 1 | 78.4 metres | 186.4 metres | 370 metres | xx patients who left the trial for ethical reasons or were treated with other medicaments

TABLE 4

| | Evaluation of some inflammation markers | | | |
|---|---|---|---|---|
| | | Placebo | Composition of example 1 | |
| Inflammation indexes | T. 0 | 3 months | 3 months | reduction |
| IL-1β (pg/ml) | 0.91 | 0.89 | 0.36* | 60.4% |
| IL-6 (pg/ml) | 1.37 | 1.36 | 1.02* | 26% |

TABLE 4-continued

Evaluation of some inflammation markers

| Inflammation indexes | Placebo | | Composition of example 1 | |
| --- | --- | --- | --- | --- |
| | T. 0 | 3 months | 3 months | reduction |
| sCD4OL | 2.47 | 2.46 | 1.39* | 43.9% |
| ESR (mm/h) | 35.64 | 37.59 | 26.3* | 26.2% |

Pharmaceutical compositions in the form of gels, creams and ointments have proved particularly useful in the topical treatment of peripheral pain and of superficial and deep inflammatory and painful conditions. The combination can be applied directly to the skin in the oil in which it is solubilised, or incorporated in creams or ointments suitable for administration. The treatment can be performed one to three times a day, applying a dose of 0.5-5 g of the topical formulation to the part of the body affected by the painful disorder.

According to a further aspect, the compositions according to the invention may be administered together with other substances having a useful or complementary activity.

The compositions according to the invention will be formulated according to conventional techniques, such as those described in "Remington's Pharmaceutical Handbook", Mack Publishing Co., N.Y., USA.

The examples below further illustrate the invention.

EXAMPLE 1

Tablets Containing Phospholipid-complexed Curcumin and Lipophilic Extract of *Echinacea*

| | |
| --- | --- |
| Phospholipid-complexed curcumin | 600.00 mg |
| *Echinacea ang.* extracted with $CO_2$ standardised to 25% isobutylamides | 5.00 mg |
| Mannitol | 345.25 mg |
| Sodium bicarbonate | 120.00 mg |
| Magnesium carbonate | 66.75 mg |
| Croscarmellose sodium | 39.00 mg |
| Silicon dioxide | 39.00 mg |
| Talc | 20.00 mg |
| Hydroxypropylcellulose | 10.00 mg |
| Magnesium stearate | 5.00 mg |
| Opadry White | 35.00 mg |
| Opadry Yellow | 15.00 mg |

EXAMPLE 2

Soft Gelatin Capsules

| | |
| --- | --- |
| Phospholipid-complexed curcumin | 300.00 mg |
| *Echinacea ang.* extracted with $CO_2$ standardised to 25% isobutylamides | 5.00 mg |
| Linseed oil | to 700 mg |

EXAMPLE 3

Tablets Containing Phospholipid-complexed Curcumin and Alcoholic Extract of *Echinacea*

| | |
| --- | --- |
| Phospholipid-complexed curcumin | 400.00 mg |
| *Echinacea ang.* alcoholic extract standardised to 1% isobutylamides | 100.00 mg |
| Mannitol | 345.25 mg |
| Sodium bicarbonate | 120.00 mg |
| Magnesium carbonate | 66.75 mg |
| Croscarmellose sodium | 39.00 mg |
| Silicon dioxide | 39.00 mg |
| Talc | 20.00 mg |
| Hydroxypropylcellulose | 10.00 mg |
| Magnesium stearate | 5.00 mg |
| Opadry White | 35.00 mg |

EXAMPLE 4

Ointment Containing Phospholipid-complexed Curcumin and Lipophilic Extract of *Echinacea angusafolia*

| | |
| --- | --- |
| Phospholipid-complexed curcumin | 200.00 mg |
| *Echinacea ang.* extracted with $CO_2$ standardised to 25% isobutylamides | 200.00 mg |
| Linseed oil | 4 g |
| Stearic acid | 12 g |
| Glycerin | 10 g |
| Cetostearyl alcohol | 2 g |
| Potassium hydroxide | 0.9 g |
| Paraben | 0.2 g |
| Demineralised water | q.s. for 100 g |

The invention claimed is:

1. Compositions for oral administration consisting of phospholipid-complexed curcumin, an extract of an *Echinacea angustifolia* and acceptable excipients, wherein the curcumin complexed with phospholipids is in an amount of 600 mg, and the *Echinacea* extract is in an amount of 5 mg, per oral unit dose.

2. Compositions according to claim 1 wherein the *Echinacea angustifolia* extract is prepared by extraction with supercritical carbon dioxide.

3. Compositions for topical administration consisting of phospholipid-complexed curcumin, an extract of an *Echinacea angustifolia* and acceptable excipients, wherein the curcumin complexed with phospholipids is in an amount of 200 mg, and the *Echinacea* extract is in an amount of 200 mg.

4. Method of treating peripheral pain, joint and muscle pain, inflammatory and superficial and deep pain conditions in patients in need thereof, said method comprising:
    administering an effective amount of the compositions according to claim 1 to said patients and
    treating said peripheral pain, joint and muscle pain, inflammatory and superficial deep pain conditions in said patients.

5. The method according to claim 4, further comprising treating osteoarthritis and rheumatoid arthritis.

\* \* \* \* \*